(12) United States Patent  (10) Patent No.: US 8,956,176 B1
Tarler  (45) Date of Patent: Feb. 17, 2015

(54) LEAD WIRE CONNECTOR FOR MEASURING ELECTROPHYSIOLOGICAL SIGNALS

(71) Applicant: Cleveland Medical Devices Inc., Cleveland, OH (US)

(72) Inventor: Matthew D. Tarler, Westlake, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 191 days.

(21) Appl. No.: 13/628,151

(22) Filed: Sep. 27, 2012

(51) Int. Cl.
*H01R 13/62* (2006.01)

(52) U.S. Cl.
USPC ......................................................... 439/370

(58) Field of Classification Search
USPC ................. 439/370, 638, 502, 352, 357–358; 29/876–877, 525, 846, 884
See application file for complete search history.

(56) References Cited

U.S. PATENT DOCUMENTS

| | | | |
|---|---|---|---|
| 4,040,697 A | 8/1977 | Ramsay et al. | |
| 4,220,387 A | 9/1980 | Biche et al. | |
| 5,944,562 A | 8/1999 | Christensson | |
| 7,083,480 B2 | 8/2006 | Silber | |
| 7,214,107 B2 | 5/2007 | Powell et al. | |
| 7,255,609 B1 | 8/2007 | Epstein | |
| 8,029,307 B2 * | 10/2011 | O'Rourke | 439/372 |
| 8,840,405 B2 * | 9/2014 | Thomas | 439/35 |
| 2009/0149731 A1 | 6/2009 | Selvitelli et al. | |
| 2009/0318009 A1 * | 12/2009 | McCauley et al. | 439/370 |
| 2013/0090000 A1 * | 4/2013 | Zhao | 439/370 |
| 2013/0235550 A1 * | 9/2013 | Stevenson et al. | 361/818 |
| 2014/0163439 A1 * | 6/2014 | Uryash et al. | 601/47 |

OTHER PUBLICATIONS

V. Mathiowitz et al., "Grip and Pinch Strength: Normative Data for Adults," Archives of physical medicine and rehabilitation, vol. 66, Issue 2, pp. 69-72, Feb. 1985. United States.
R. G. et al., "External finger forces in submaximal five-finger static pinch prehension," Ergonomics, vol. 35, Issue 3, pp. 275-288, Mar. 1992. England.
Spes Medica English Product Catalog, p. 41.

* cited by examiner

*Primary Examiner* — Jean F Duverne
(74) *Attorney, Agent, or Firm* — Brian Kolkowski

(57) ABSTRACT

The present invention is related to a connector for a lead wire for a electrode. The present invention is further related to the use of a connection element to provide mechanical and electrical connections with a physiological electrode. The present invention is further related to the use of a helical connection element to provide mechanical and electrical connections with the node of a physiological electrode. In various embodiments, the invention comprises an expander that can stretch the connection element so that it may fit over the head of a male connector of an electrode and release to secure the connection element around the neck of the male connector of the electrode. When secured to the electrode, the connection element preferably makes contact with the electrode at multiple points in order to increase electrical connectivity with the electrode and decrease mechanical force in a single direction on the electrode.

6 Claims, 10 Drawing Sheets

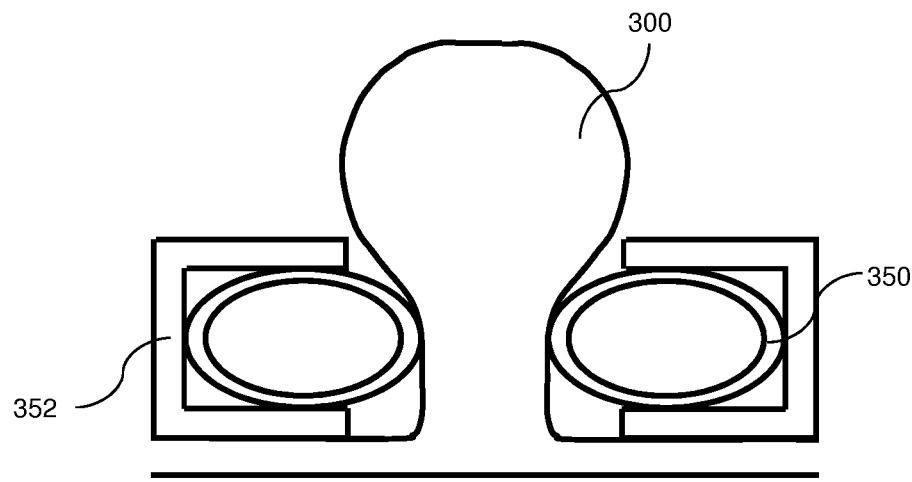
*FIG. 8a*
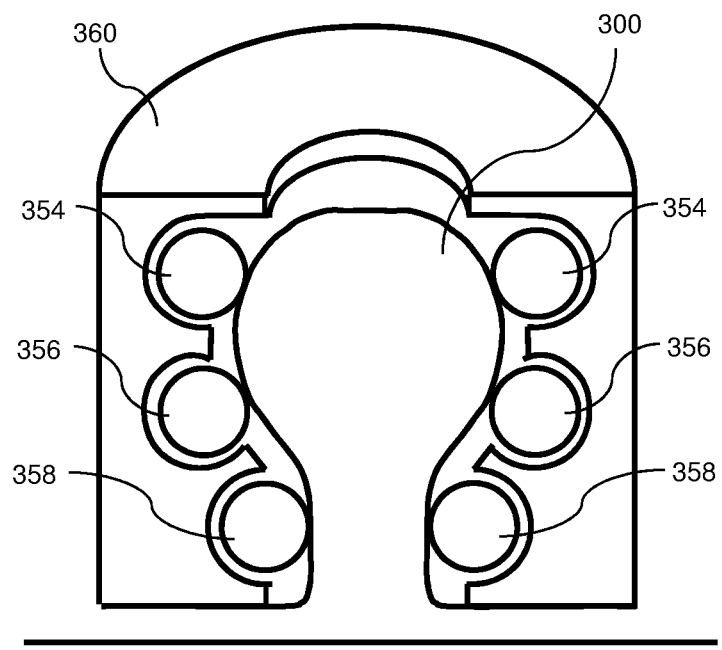
*FIG. 8b*
*FIG. 8*

LEAD WIRE CONNECTOR FOR MEASURING ELECTROPHYSIOLOGICAL SIGNALS

STATEMENT REGARDING FEDERALLY SPONSORED RESEARCH OR DEVELOPMENT

The U.S. Government has a paid-up license in this invention and the right in limited circumstances to require the patent owner to license others on reasonable terms provided for by the terms of grant number 2R44NS053116 from the National Institutes of Health, National Institute of Neurological Disorders and Stroke.

BACKGROUND OF THE INVENTION

1. Field of Use

The present invention is related to a connector for a lead wire for an electrode. The present invention is further related to the use of a connection element to provide mechanical and electrical connections with a physiological electrode. The present invention is further related to the use of a helical connection element to provide mechanical and electrical connections with the node of a physiological electrode. In various embodiments, the invention comprises an expander that can stretch the connection element so that it may fit over the head of a male connector of an electrode and release to secure the connection element around the neck of the male connector of the electrode. When secured to the electrode, the connection element preferably makes contact with the electrode at multiple points in order to increase electrical connectivity with the electrode and decrease mechanical force in a single direction on the electrode.

2. Technology Review

Electrodes for measuring biopotentials are used extensively throughout the research and clinical healthcare industries. Applications include electrocardiography, electroencephalography, electrical impedance tomography, electromyography, electrooculography, and the like. In order for these electrodes to work, they must be connected to lead wires that can carry their recorded biopotential signals to a physiological monitoring device for appropriate processing. The connection between these electrodes and lead wires is therefore a crucial factor in the successful recording of biopotentials.

Most current electrode lead wires on the market employ a "snap" connector for attaching the lead wire to an electrode. As the name implies, these lead wire connectors snap, like a button, onto the electrode node. In order to snap on, these connectors require a considerable amount of downward force applied by the clinician, usually after the electrode has been attached to the subject, in order to make the connection. Such force can be uncomfortable to a subject, as in being poked, pinching hair between the connector and electrode, pulling skin, and the like. When the snapping force is in a different direction, the result can be ripping off an electrode attached to a subject. Furthermore, once connected to an electrode, the snap connectors do not result in tight mechanical connections. Usually only one or two points of contact are made between the lead wire connector and electrode node causing poor electrical connectivity, increased electrical noise, and motion artifact. In some instances, the weight of the lead wire connector can be uncomfortable to a subject or even cause an attached electrode to rip off a subject.

Others in the field have developed lead wire connectors to overcome many of the above problems, but these too have drawbacks. For example, many current technologies make use of biasing elements to control the size of an opening that an electrode node can fit in. In this way, the opening can be enlarged so that there is no force on the electrode during application of the lead wire connector. When the opening is closed, the lead wire connector is contracted and locked into place around the electrode node. While these technologies solve many of the force problems of snap connectors, they are still limited in the number of electrical contact points between the electrode and lead wire connector due to rigidity of the connection points in the opening of the lead wire connector. Furthermore, many of these lead wire connectors are complicated structures that are large or heavy and result in the same detached electrodes or discomforts to a subject mentioned above. Such complicated structures with poor force distribution can also lead to catastrophic failure of the biasing elements and lead wire connector.

Still others have attempted to correct the electrical connection problem by using a spring to create a form fitting connection between the lead wire connector and electrode. This technology, however, provides clinicians with the same difficulties as snap connectors: pushing, pulling, pinching, and the like because there is no biasing element for expanding the spring.

It is therefore an object of the present invention to create a lead wire connector that may be applied to an electrode without excess force. It is further an object of the present invention to create a lead wire connector with a better electrical connection to the electrode than the current art. It is further an object of the present invention to create a lead wire connector that utilizes the biasing properties of a spring connection element in a way that increases its ease of application over current art. It is still further an object of the present invention to create a lead wire connector that is comfortable for a subject to wear. It is still further an object of the present invention to create a lead wire connector that may be used in both research and clinical settings.

SUMMARY OF THE INVENTION

The present invention is related to a connector for a lead wire for a electrode. The present invention is further related to the use of a connection element to provide mechanical and electrical connections with a physiological electrode. The present invention is further related to the use of a helical connection element to provide mechanical and electrical connections with the node of a physiological electrode. In various embodiments, the invention comprises an expander that can stretch the connection element so that it may fit over the head of a male connector of an electrode and release to secure the connection element around the neck of the male connector of the electrode. When secured to the electrode, the connection element preferably makes contact with the electrode at multiple points in order to increase electrical connectivity with the electrode and decrease mechanical force in a single direction on the electrode.

In certain preferred embodiments of the present invention, a lead wire connector is used to establish mechanical and electrical connections between a lead wire and an electrode. The size of the connector is able to increase and decrease so that it may be slipped over and contracted around the head of an electrode without applying excess force to either a subject or an electrode attached to the subject. In many preferred embodiments, this is accomplished by pinching an expander attached to a connection element in such a way that the pinching overcomes the internal biases of the connection element and enlarges the lead wire connector. When pinching is released, the internal biases of the connection element and expander contract the lead wire connector. Certain other embodiments, however, use a sliding mechanism to overcome internal biases and alter the size of the opening of the connection element.

Additionally, certain preferred embodiments of the present invention use a spring or spring like element to create the connection element of the lead wire connector. A spring may be stretched in both regular and irregular shapes to conform to any electrode shape. Furthermore, each loop of a spring provides a contact point with an electrode that may be used to increase electrical connectivity.

A number of embodiments of the present invention are envisioned in this disclosure. The following embodiments are examples of the many embodiments encompassed by the present invention, but do not in any way limit the many other embodiments covered by this disclosure.

In one embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the connection element is further preferably in continuous contact with the node of the male connector.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the electrode containing the node of the male connector is a physiological electrode.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the expander for stretching the connection element overcomes an internal bias of the connection element.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the expander for stretching the connection element is attached to the connection element at least at 2 points.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the lead wire connector comprises at least 2 connection elements.

In still another embodiment, the present invention includes a lead wire connector comprising a connection element; and an expander for stretching the connection element, wherein the connection element can be slipped over a node of a male connector and placed in contact at least at 5 separate points with the node of the male connector without applying substantial force in any direction to an electrode containing the node of the male connector, and the connection element creates both a mechanical and electrical connection with the node of the male connector.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the helical connection element is further preferably in continuous contact with the node of the male connector.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the electrode containing the node of the male connector is a physiological electrode.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the expander for stretching the helical connection element overcomes an internal bias of the helical connection element.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the expander for stretching the helical connection element is attached to the helical connection element at least at 2 points.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the lead wire connector comprises at least 2 helical connection elements.

In yet another embodiment, the present invention includes a lead wire connector comprising a helical connection element; and an expander for stretching the helical connection element, wherein the helical connection element can be slipped over a node of a male connector and placed in contact at least at 5 separate points with the node of the male connector without applying substantial force in any direction to an electrode containing the node of the male connector, and the connection element creates both a mechanical and electrical connection with the node of the male connector.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode, and the connection element is helical.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode, and the connection element makes continuous contact with the node of the male connector of the electrode.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode, and the expander applies a multidirectional force to stretch at least 2 connection elements.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode, and the electrode is a physiological electrode.

In still yet another embodiment, the present invention includes a method for connecting at least one lead wire to an electrode comprising applying a unidirectional or bidirectional force to an expander which in turn applies a multidirectional force to stretch a connection element for receiving a node of a male connector of the electrode; placing the connection element for receiving the node of a male connector of the electrode over the node of the male connector of the electrode; and releasing the unidirectional or bidirectional force on the expander in order to contract the connection element around the node of the male connector of the electrode, wherein the connection element contracts to make contact at least at 5 separate points with the node of the male connector of the electrode, and there is no vector sum of forces on the electrode.

BRIEF DESCRIPTION OF THE FIGURES

FIG. 8 Cross section of the electrode connector of the present invention with a (a) single and with (b) multiple connector elements.

DESCRIPTION OF THE PREFERRED EMBODIMENTS

Figure 1:
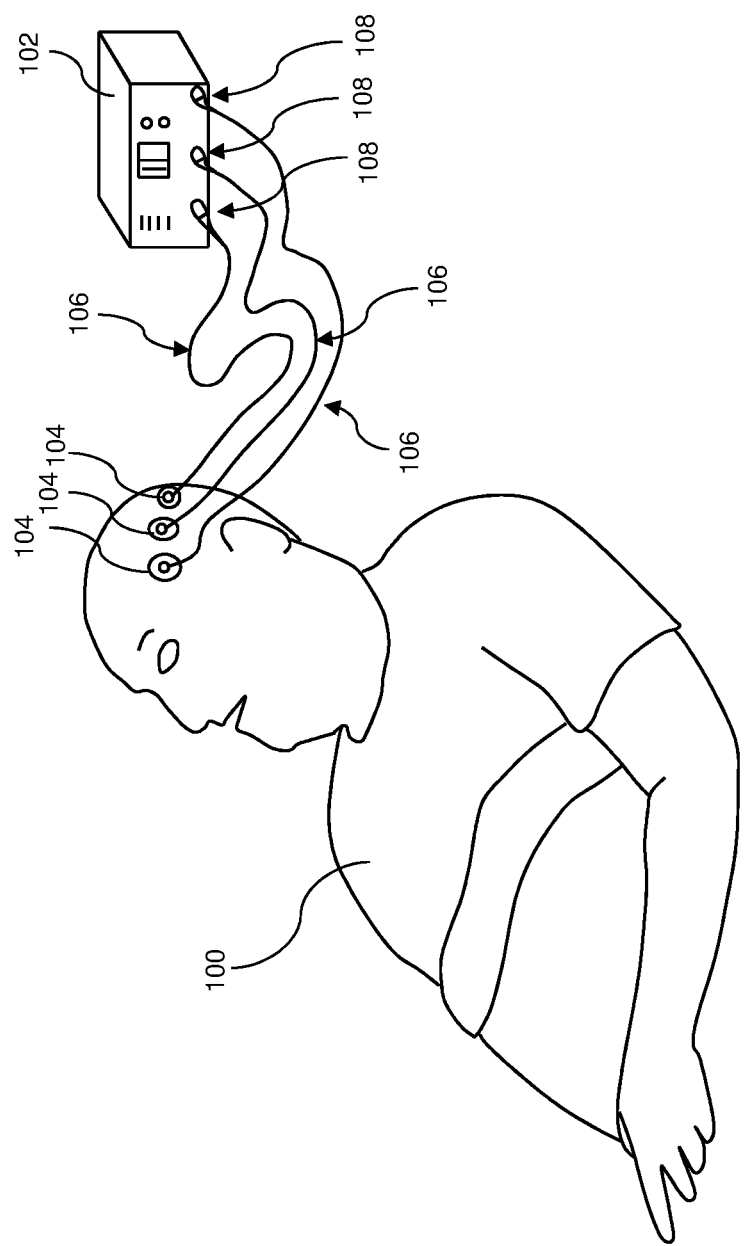
FIG. 1 Illustration of subject wearing electrodes attached to lead wires using the connector of the present invention.

The present invention is related to a connector for a lead wire for a electrode. The present invention is further related to the use of a connection element to provide mechanical and electrical connections with a physiological electrode. The present invention is further related to the use of a helical connection element to provide mechanical and electrical connections with the node of a physiological electrode. In various embodiments, the invention comprises an expander that can stretch the connection element so that it may fit over the head of a male connector of an electrode and release to secure the connection element around the neck of the male connector of the electrode. When secured to the electrode, the connection element preferably makes contact with the electrode at multiple points in order to increase electrical connectivity with the electrode and decrease mechanical force in a single direction on the electrode. While the following detailed description describes preferred embodiments of a lead wire connector for an electrode, it is to be understood that these embodiments are merely exemplary and are not inclusive of every device or method within the scope of the present invention.

Various embodiments of the present invention include the use of a connection element, preferably helical in design, in part to create an electrical connection between an electrode and lead wire. Because the connection element is in part used to make an electrical connection, the connection element should at least in part be made of a conductive material. Conductive materials can include copper, nickel, aluminum, steels, alloys, or the like. Other conductive non-traditional materials may be used as well. These include conductive polymers, conductive coatings, electroceramics, and the like. Preferably only the external surface of the connection element makes contact with the electrode. Therefore a material may be chosen specifically for its mechanical properties, even if non-conductive, such as a polymer or steel, to provide the desired structural base for the connection element. The base material of the connection element may then be coated or plated with a conductive material to provide the connection element with its desired electrical properties. Additionally, the connection element should have a shape capable of slipping over the head of a male connector of an electrode (i.e. round), hereinafter an electrode head, and be flexible so as to conform to that shape and/or the neck of a male connector of an electrode, hereinafter an electrode neck, located at the based of the electrode head. By conforming its shape to an electrode head and/or neck, the connection element will have many separate contact points with the electrode and therefore not apply substantial force in any direction on the electrode. As the number of contact points between the connection element and the electrode increases, electrical resistance will decrease resulting in a better electrical connection. For purposes of this invention, a contact point is any location on the electrode in contact with the connection element. Preferably the connection element will contact the electrode at least at 3 separate points; more preferably, the connection element will contact the electrode at least at 5 separate points; even more preferably, the connection element will contact the electrode at least at 7 separate points; still more preferably, the connection element will contact the electrode at least at 10 separate points; still even more preferably the connection element will contact the electrode at least at 15 points; still even more preferably the connection element will contact the electrode at least at 20 points; still even more preferably the connection element will contact the electrode at least at 25 points; still even more preferably the connection element will contact the electrode at least at 35 points; still even more preferably the connection element will contact the electrode at least at 50 points; most preferably, the connection element will be in continuous contact with the electrode.

Various embodiments of the present invention also include an expander for enlarging the shape of the connection element. The expander allows the connection element to easily slide over the electrode head without detaching or applying too great a force to the electrode. The expander is preferably a similar shape to that of the connection element and electrode (i.e. round) and preferably attached to the connection element in at least one point. The expander is also preferably made from a lightweight and insulating material capable of elastic deformation such as rubbers, certain plastics, other polymers, and the like. By being lightweight, the expander does not cause excess stress on a subject or the electrode. By being insulating, the mechanical and electrical connections between the electrode, connection element, and lead wire are insulated from the user and subject. Such insulation results in greater comfort for the subject by preventing pinching, hair pulling, and hard and sharp contact with skin. Insulation also creates a stronger electrical signal between the electrode and lead wire by increasing conductivity, thereby increasing the signal to noise ratio between the lead wire connector and electrode and decreasing current leak between the lead wire connector and the environment. By being elastic, the expander has an internal bias so that it can maintain its shape around the head of the electrode and operate in a manner described below. Although elastic, the expander is also stiff enough to maintain its shape against an internal bias force from an attached connection element. In certain embodiments, however, a rigid material can be used when the mechanism of action of the expander does not require flexibility. Furthermore, the expander preferably has at least one operational point, such as a pinch point, where force can be applied or released by a user to operate the expander thereby overcoming its internal bias and/or the internal bias of the connection element. For example, in certain embodiments where the expander and connection elements are round, an applied force would enlarge the diameter of both elements and releasing the applied force would decrease the diameter of both elements. It should be clear that the shape of both the expander and connector elements may be any shape, even irregular, and are not limited to round, oval, or circular in nature.

For the expander and connection elements to operate in unison via user applied force at an operational point, in certain specific embodiments of the present invention the connection element is attached to the expander in a number of locations. Therefore, as the internal bias of the expander is overcome by the user applied force and the expander enlarges, the connection element also enlarges in a substantially similar way. In certain other embodiments, force applied at an operational point operates to overcome only the internal bias of the connection element. For example, certain embodiments of an expander that resemble a bolo tie, zipper, or the like, operate by sliding up and down the connection element. This motion, while not directly affecting the internal bias of the expander, does affect the internal bias of the connection element so as to enlarge or contract the opening created by the shape of the connection element. In certain other embodiments, an additional biasing element is used to either enhance the internal bias effect of either the expander or the connection element. For example, in various preferred embodiments, a force to overcome the internal bias of the expander is applied at two operational points by a pinch with the thumb and index finger. The addition of a spring between the two pinch points enhances the effect of the internal bias of the expander. Preferably the force required to overcome the internal bias of the expander and connection element is less than 50 Newtons; more preferably the force required to overcome the internal bias effect of the expander and connection element is less than 25 Newtons; even more preferably the force required to overcome the internal bias effect of the expander and connection element is less than 10 Newtons; still more preferably the force required to overcome the internal bias effect of the expander and connection element is less than 7 Newtons; still even more preferably the force required to overcome the internal bias effect of the expander and connection element is less than 5; still even more preferably the force required to overcome the internal bias effect of the expander and connection element is less than 3; still even more preferably the force required to overcome the internal bias effect of the expander and connection element is less than 1 Newton; still even more preferably the force required to overcome the internal bias effect of the expander and connection element is less than 0.5 Newtons.

In various embodiments, preferably the expander should enlarge the connection element without requiring a substantial applied force so that it may be placed over the electrode head without creating any contact points until force is removed and the expander and connection element contract. For purposes of this invention, a substantial applied force is considered to be a greater than average non-ergonomic force as known to those skilled in the art. It is important to prevent the creation of contact points until the expander and connection element have been placed over the electrode head to prevent premature mechanical and electrical connections with the electrode that might cause an attached electrode to detach from a subject or cause injury or discomfort to a subject. By premature mechanical connection it is meant that each contact point on the electrode receives a force due to the internal bias of both the expander and connection element as well as any force resulting from the user placing the expander and connection element over the electrode; when the vector sum of these forces is not equal to zero, the force on the electrode is unbalanced. If these forces are not properly balanced in all directions, often the result of premature contact, the result can be uncomfortable to a subject by pinching hair, applying extreme pressure, detaching an electrode already applied to the subject, and the like. By premature electrical connection it is meant that contact points between the connection element and electrode cause the transmission of an electrical signal before the entirety of the system is properly insulated and connected, thus causing potentially hazardous conditions for a subject and poor signal transmission. Turning now to a description of the figures. FIG. 1 illustrates a general use for various preferred embodiments of the present invention. In FIG. 1, a physiological monitoring device 102 is used to record physiological data from a subject 100. Lead wires 106 carry recorded electrical signals from electrodes 104 located on the subject's 100 head to the physiological monitoring device 100. While FIG. 1 shows electrodes 104 located on a subject's 100 head, it should be noted that the present invention may be used for electrodes located anywhere capable of measuring an electrical signal, preferably a physiological signal. The lead wire connectors of the present invention (not presently shown in detail, but illustrated throughout the remaining figures) connect the electrodes 104 to the lead wires 106. Form fitting plugs 108 or other types of connectors connect the opposite end of the lead wires 106 to the physiological monitoring device 102. It can be seen from FIG. 1 that the connector of the present invention preferably creates strong electrical and mechanical connections, and is comfortable for the subject.

Figure 2:
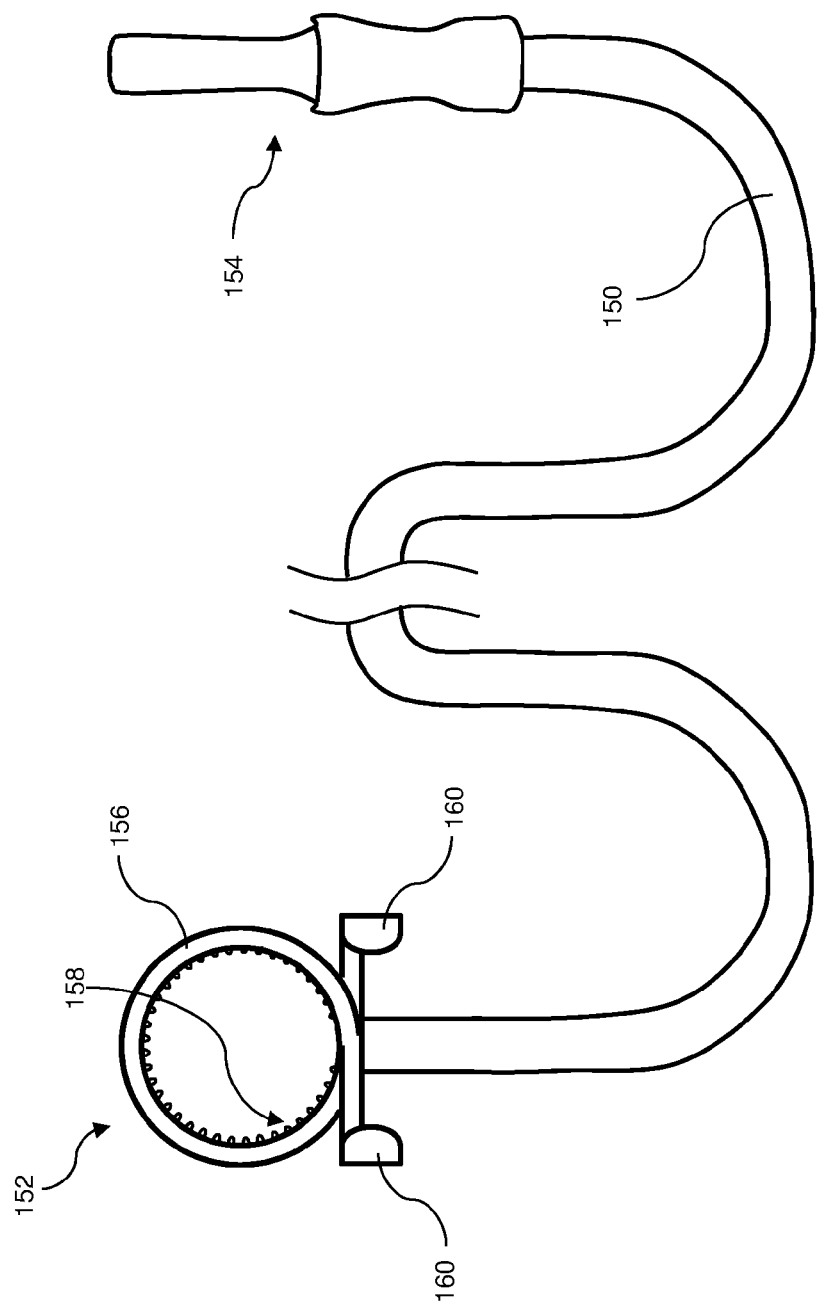
FIG. 2 Illustration of electrode lead wire including connector of the present invention.

FIG. 2 is an illustration of the entirety of an electrode lead including the lead wire 150, the lead wire connector of the present invention 152 for connecting the lead wire 150 to an electrode (not shown), and a form fitting plug 154 or other connector for attaching the electrode lead to a recording device. The embodiment of the lead wire connector 152 shown in FIG. 2 illustrates a round connection element 158 located inside a round expander 156. Additionally, the expander 156 contains two operational points 160—pinch points—at its base that may be pinched by a user between his fingers or like action to generate a force that overcomes the internal bias of the expander 156 and connection element 158. When a force is applied to the pinch points 160, the circumference of both the expander 156 and connection element 158 of the lead wire connector 152 enlarge, allowing the user, presumably a clinician, to slip the lead wire connector 152 over an electrode head (not shown). The applied force at the pinch points 160 overcomes the internal bias of the expander 156 and connection element 158 thereby allowing both to enlarge. When force on the pinch points 160 is released, the circumference of both the expander 156 and connection element 158 of the lead wire connector 152 contract around the electrode head and/or electrode neck to create mechanical and electrical connections. This contraction is a result of the internal biases of both the expander 156 and connection element 158.

Figure 3:
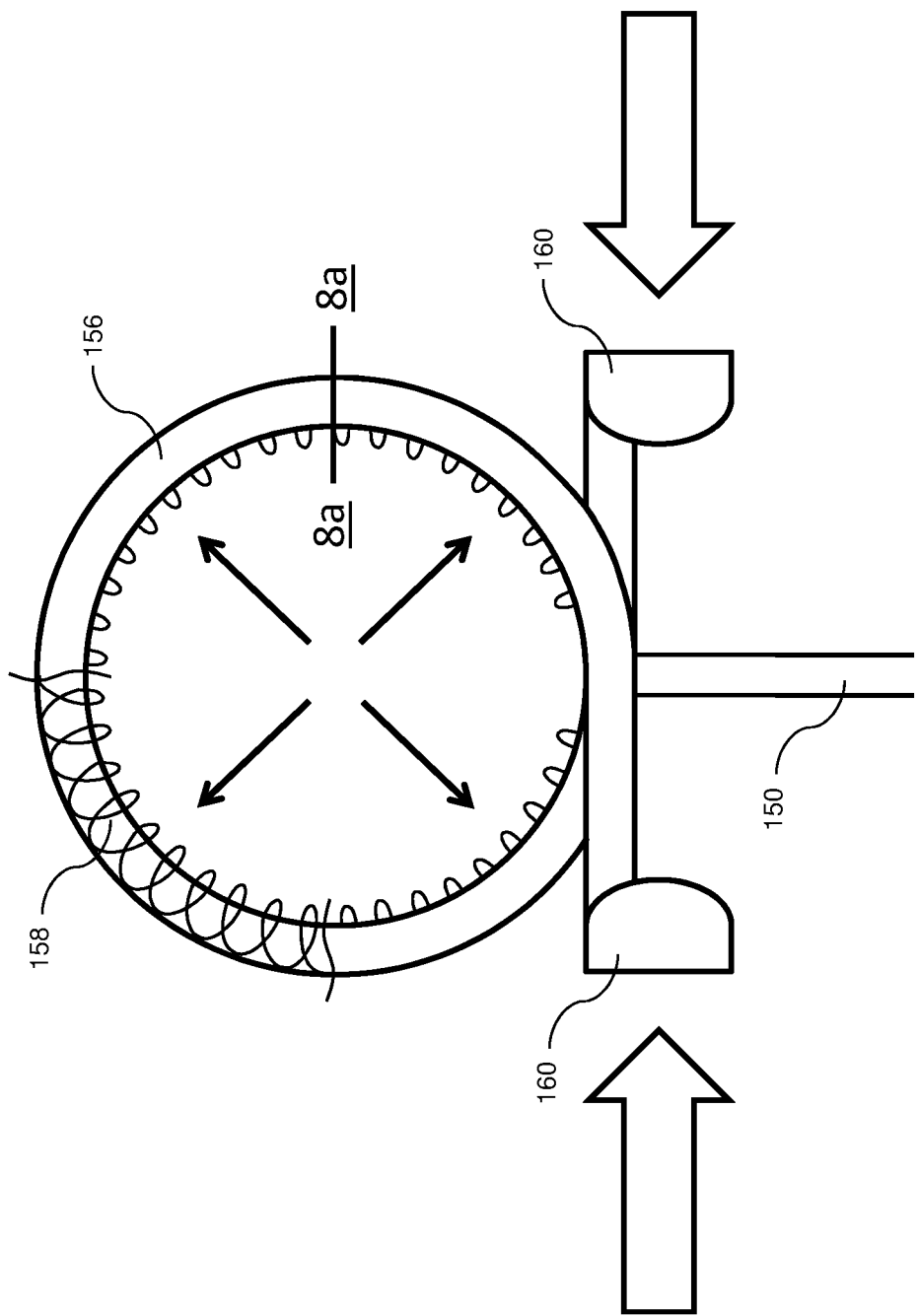
FIG. 3 An exemplary embodiment of the electrode connector of the present invention.

FIG. 3 shows in more detail a similar embodiment of the lead wire connector shown in FIG. 2. The lead wire connector shown in FIG. 3 has both an expander 156 and connection element 158. A cutaway of the expander 156 is shown in its upper left quadrant to reveal a helical nature to the connection element 158 contained inside. This helical nature, like a spring, provides the connection element 158 at least in part with its internal bias necessary to contract with the expander 156. In certain embodiments, the base of some or all of the loops of the spring of the connection element 158 are attached to the expander 156 so that as the expander 156 expands and contracts, the connection element 158 expands and contracts in a substantially similar manner. Furthermore, the external surface of the connection element 158 is preferably conductive so as to create an electrical connection with an electrode (not shown) and be able to transmit signals from any contact point to the lead wire 150. While the connection element 158 is shown in FIG. 3 as a spring, it is to be understood that the connection element 158 may be of any functional structure that accomplishes the goals of the present invention. Furthermore, while FIG. 3 illustrates a lead wire connector of a round shape, it is to be understood that the lead wire connector may be of any shape, regular or irregular, substantially similar to that of the electrode.

The embodiment of the lead wire connector shown in FIG. 3 is preferably operated by manually operating the expander 156 at the operational points 160. Two operational points—pinch points 160—are located at the base of the lead wire connector. Force to these pinch points 160, preferably a pinch between fingers, causes the distance between them to decrease as shown. As the distance between pinch points 160 decreases, preferably the diameter of the opening of the expander 156 and connection element 158 increases as shown in a substantially similar manner to each other. With an enlarged opening, the lead wire connector of the present invention is preferably slipped over an electrode head. As the pinch points 160 are released, the expander 156 and connection element 158 preferably contract around the electrode head and/or neck resulting in a multiple contact points between the connection element 158 and electrode. In the embodiment of the present invention as shown in FIG. 3, the number of contact points is determined by the number of loops of the connection element's 158 spring. In other embodiments of the present invention, the number of contact points is determined by the number protrusions of the connection element 158 into the opening of the lead wire connector.

Figure 4:
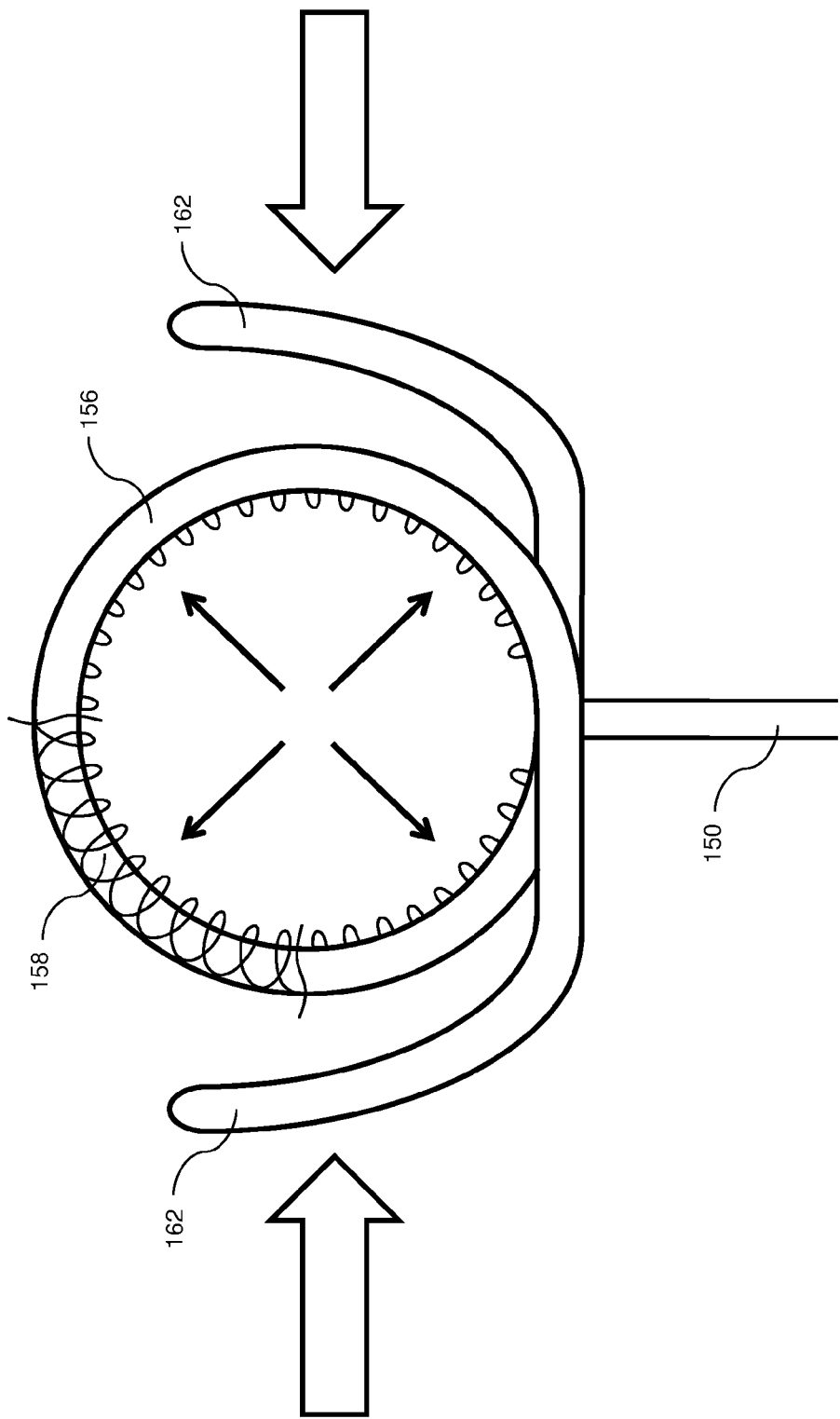
FIG. 4 An exemplary embodiment of the electrode connector of the present invention.

FIG. 4 illustrates a different embodiment of the present invention. The operational points 162 of FIG. 4, also pinch points similar to those in FIG. 3, are located near the middle of the lead wire connector. While the location of the pinch points 162 differs, their function is preferably the same as that described in FIG. 3. The connection element is also electrically connected to the lead wire 150 so that once contact is made between the connection element 158 and electrode, an electrical signal may be sent from the electrode to the lead wire as described in FIG. 1.

Figure 5:
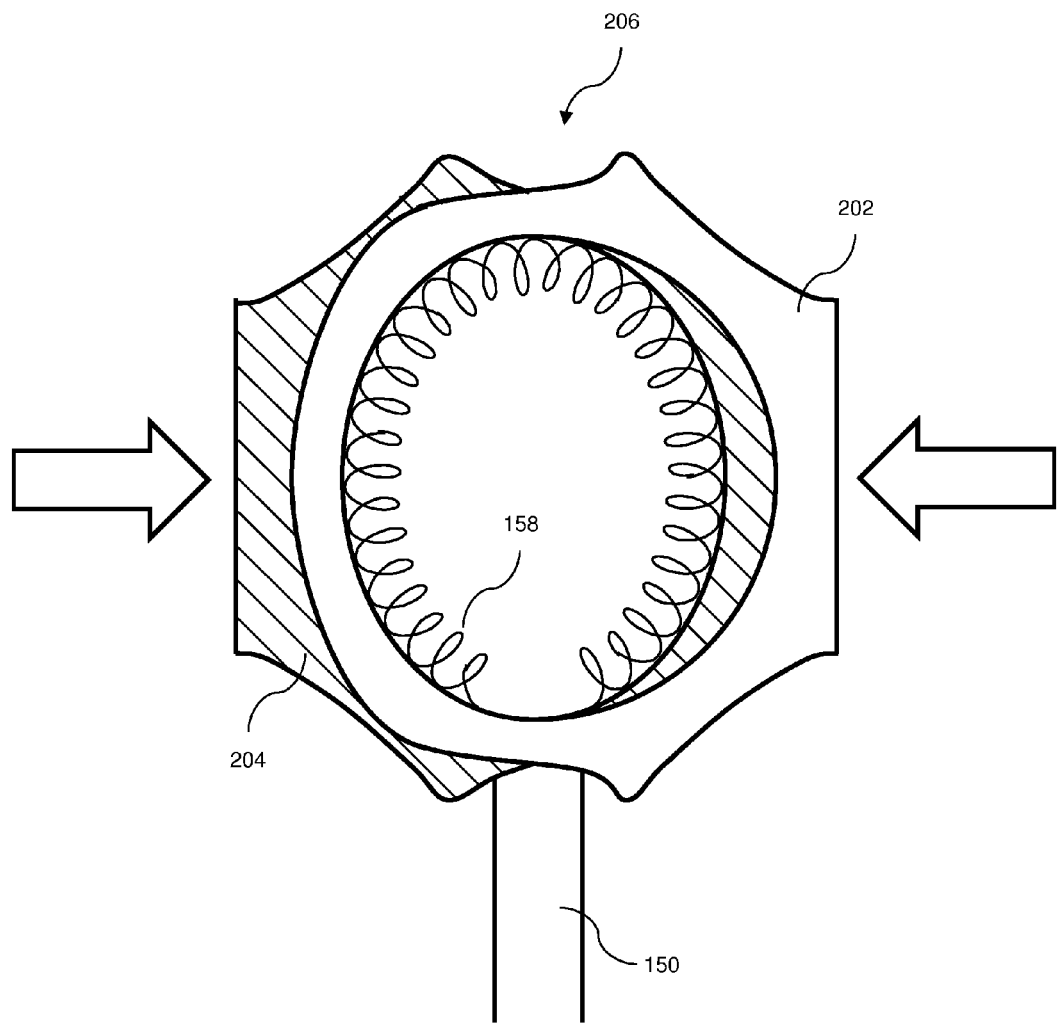
FIG. 5 An exemplary embodiment of the electrode connector of the present invention.

FIG. 5 illustrates another preferred embodiment of the lead wire connector of the present invention. Similar to previously described embodiments, the connection element 158 is helical and spring-like, and connected to an upper expander 206. The connection element 158 is preferably one that matches the previous descriptions. The expander 206 of the embodiment in FIG. 5, however, comprises an upper segment 202 and a lower segment 204 where the upper segment 202 is similar to the lower segment 204 but rotated 180 degrees. Preferably the connection element 158 is connected to both the upper segment 202 and lower segment 204 of the expander 206 but on opposite sides so as to hold the two segments 202, 204 together and allow the connection element 158 to expand with the expander 206 in a substantially similar manner. In the embodiment shown in FIG. 5, force is preferably applied to both the upper segment 202 and lower segment 204 of the expander 206 so as to slide them over each other and increase the overlapping area of the openings of both the upper segment 202 and lower segment 204, thereby expanding the connection element 158. As this force is applied, the connection element 158 is preferably stretched by both the upper segment 202 and lower segment 204 of the expander 206 in a manner that overcomes the connection element's 158 internal bias. When the applied force is release, the internal bias of the connection element 158 causes the lead wire connector to contract around an electrode head and/or electrode neck. Like in other embodiments, the connection element 158 is electrically connected to a lead wire 150 so that an electrical signal may be sent from the electrode through the lead wire as described in FIG. 1.

Figure 6:
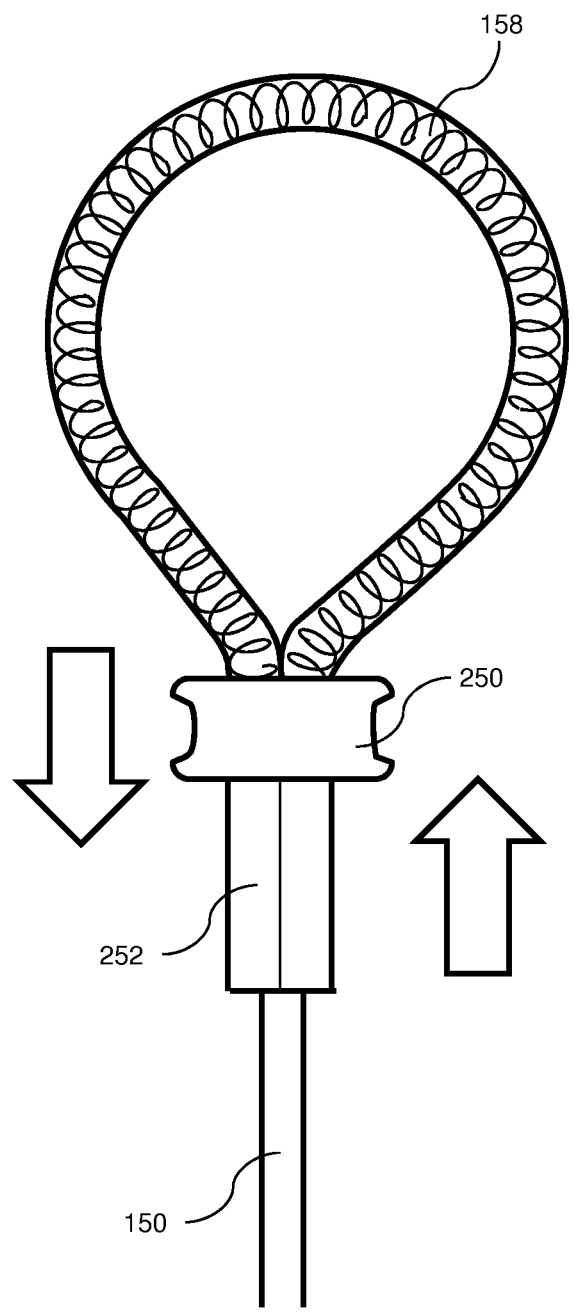
FIG. 6 An exemplary embodiment of the electrode connector of the present invention.

FIG. 6 illustrates yet another embodiment of the present invention. In this embodiment, the connection element 158 is yet again preferably a helical shape and similar to a spring, however, it may be of any shape or material that is capable of providing multiple points of contact to an electrode, conforming its shape to the electrode, and creating an electrical connection between the electrode and lead wire 150. Rather than using pinch points as in the embodiments described above, the embodiment of FIG. 6 preferably uses a bolo tie or zipper like expander. The operational point 250 is preferably located at the base of the lead wire connector and preferably slides up and down a track 252 due to an applied force. As the operational point 250 is forced down the track 252, the area enclosed by the connection element 158 increases, thus allowing the lead wire connector to be slipped over an electrode head. As the operational point 250 is forced back up the track 252, the area enclosed decreases and tightens around the electrode head so that the connection element 158 makes multiple contact points with the electrode. In each of the above actions, the expander acts on the internal bias of the connection element 158, rather than its own internal bias. As previously described, the connection element 158 is preferably electrically connected to the lead wire 150 so that an electrical signal may be sent from the electrode through the lead wire 150 as described in FIG. 1.

Figure 7:
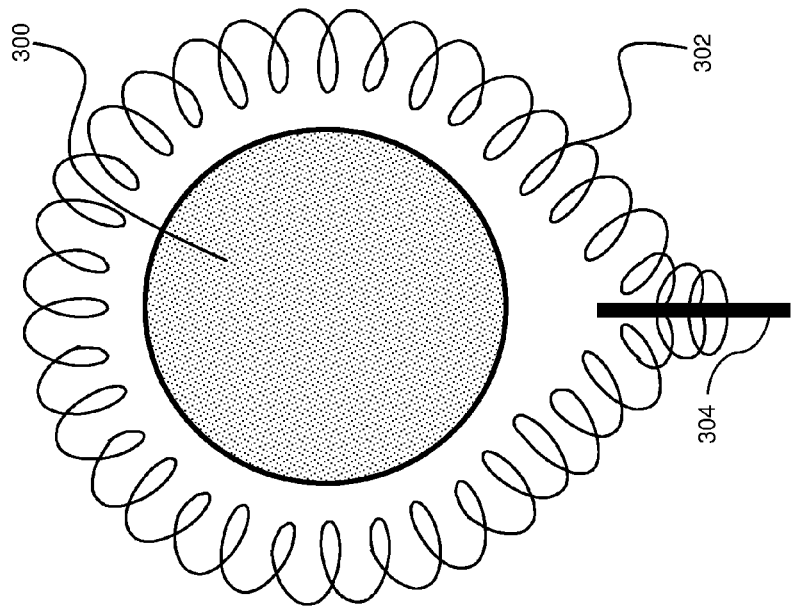
FIG. 7a-b Illustrations of the mechanical and electrical connections between the electrode connector of the present invention and an electrode node in the (a) closed and (b) open configurations.
Figure 7:
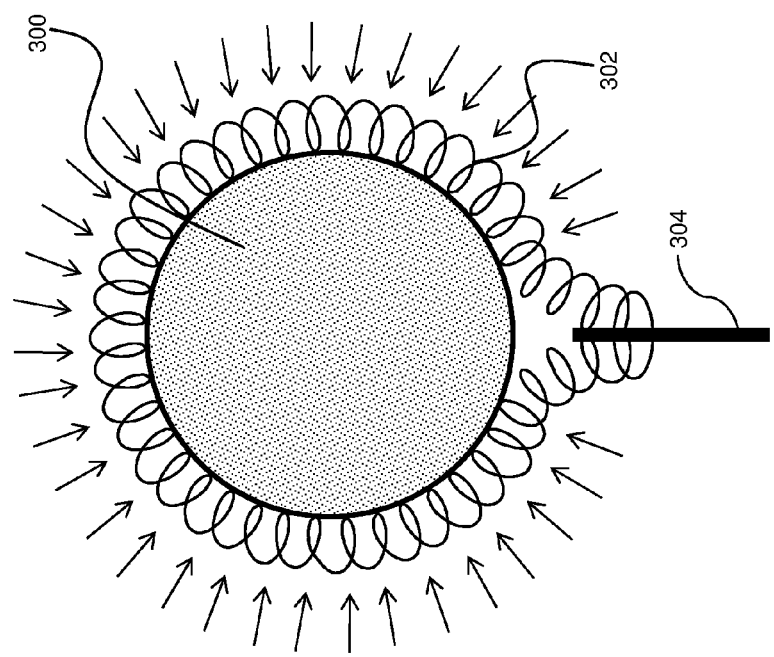

FIG. 7 illustrates a connection element 302 around an electrode node 300 in the (a) closed position, and (b) open position. Preferably, each loop of a spring connection element 302, or similar protrusion, creates a contact point with the electrode node 300 as shown in FIG. 7a by substantially altering its shape to that of the electrode node 300. The connection element 302 is conductive such that an electrical signal transmitted from the electrode node 300 through any contact point with the connection element 302 is also transmitted to the lead wire 304. Therefore, the increase in electrical contact points decreases electrical resistance and noise. Furthermore, the force applied to the electrode node 300 due to the internal biases of the expander (not shown) and connection element 302 is preferably distributed as shown in multiple directions. Conversely, as shown in FIG. 7b, when the connection element is open, as when slipped over the electrode node 300, there is preferably no contact or minimal contact between the connection element 302 and the electrode node 300. With no connection points, there may be no electrical transmission of signals or mechanical forces between the connection element 302 and electrode node 300.

FIG. 8 illustrates the relationship between a connection element and expander around an electrode node in two embodiments of the present invention. FIG. 8a first illustrates the relationship with a single connection element 350 directly attached to an expander 352. The connection element 350 is preferably attached to the expander 352 at the top, bottom, and one side, while the fourth side protrudes past the end of the expander 352. During operation, the expander 352 and connection element 350 are preferable stretched so as to increase the distance antipodes such that the expander 352 and connection element 350 are capable of fitting over the electrode node 300. As the expander 352 reaches the base of the electrode node 300, the expander 352 preferably contracts so the distance between antipodes decreases and contact is made between the connection element 350 and the neck of the electrode node 350. FIG. 8b preferably operates in much the same way, except there are preferably multiple connection elements 354, 356, 358. Furthermore, the expander 360 preferably contains multiple pockets for each connection element 354, 356, 368.

Figure 9:
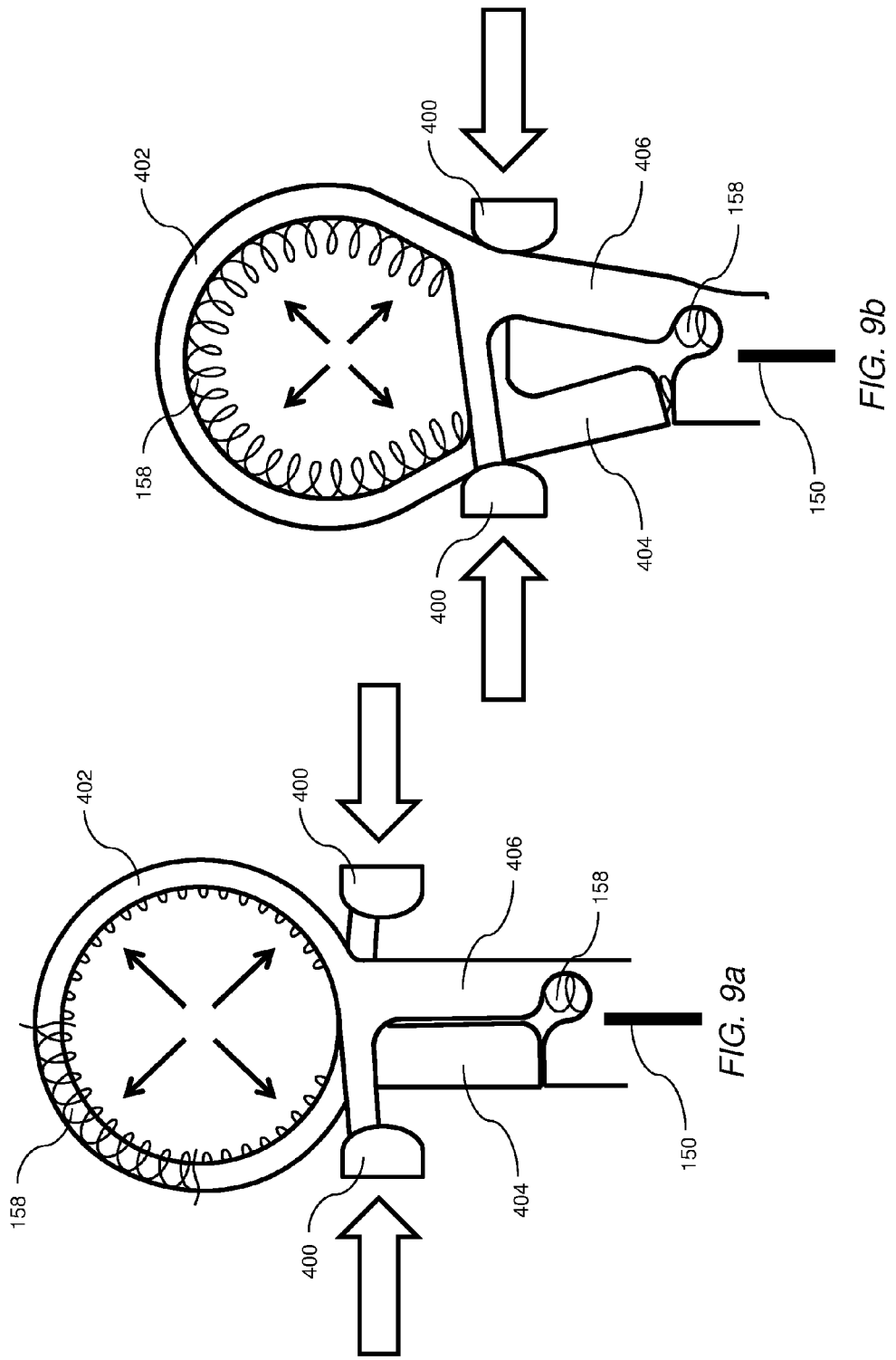
FIG. 9a-b An exemplary embodiment of the electrode connector of the present invention.

Finally, FIG. 9 illustrates yet another embodiment of the present invention in the (a) closed position, and (b) open position. Much like FIG. 3, the embodiment of FIG. 9 contains two operational pinch points 400 used to expand and contract an expander 402 as previously described. A connection element 158 is also preferably helical in nature and has the same mechanical and electrical properties as previously. Unlike FIG. 3, however, the connection element 158 connects to a lead wire 150 which itself is stationary and connected at the base of the expander 402. By attaching the lead wire 150 to the expander 402 in this manner, the lead wire 150 cannot affect the internal bias of the connection element 158 in a manner opposite that of the expander 402. The expander 402 preferably contains a left base compartment 404 and a right base compartment 406 that are both capable of containing the connection element 158.

In FIG. 9a, when the expander 402 is closed, the left base compartment 404 and right base compartment 406 are located next to each other. In FIG. 9b, however, as the operational pinch points 400 are pressed together, the left base compartment 404 and right base compartment 406 rotate away from each other about a pivot point near the attachment of the lead wire 150 to the expander 402. By pivoting away from each other, the connection element 158 contained within both base compartments 404, 406 is stretched, overcoming its internal bias, along with the expander 402, thereby enlarging the opening for an electrode to fit inside. When the lead wire connector is slipped over an electrode and the operational pinch points 400 are released, the base compartments 404, 406 return together due to the internal biases of the expander 402 and connection element 158. This movement contracts the lead wire connector around the electrode and returns it to the configuration shown in FIG. 9*a*.

Figure 10:
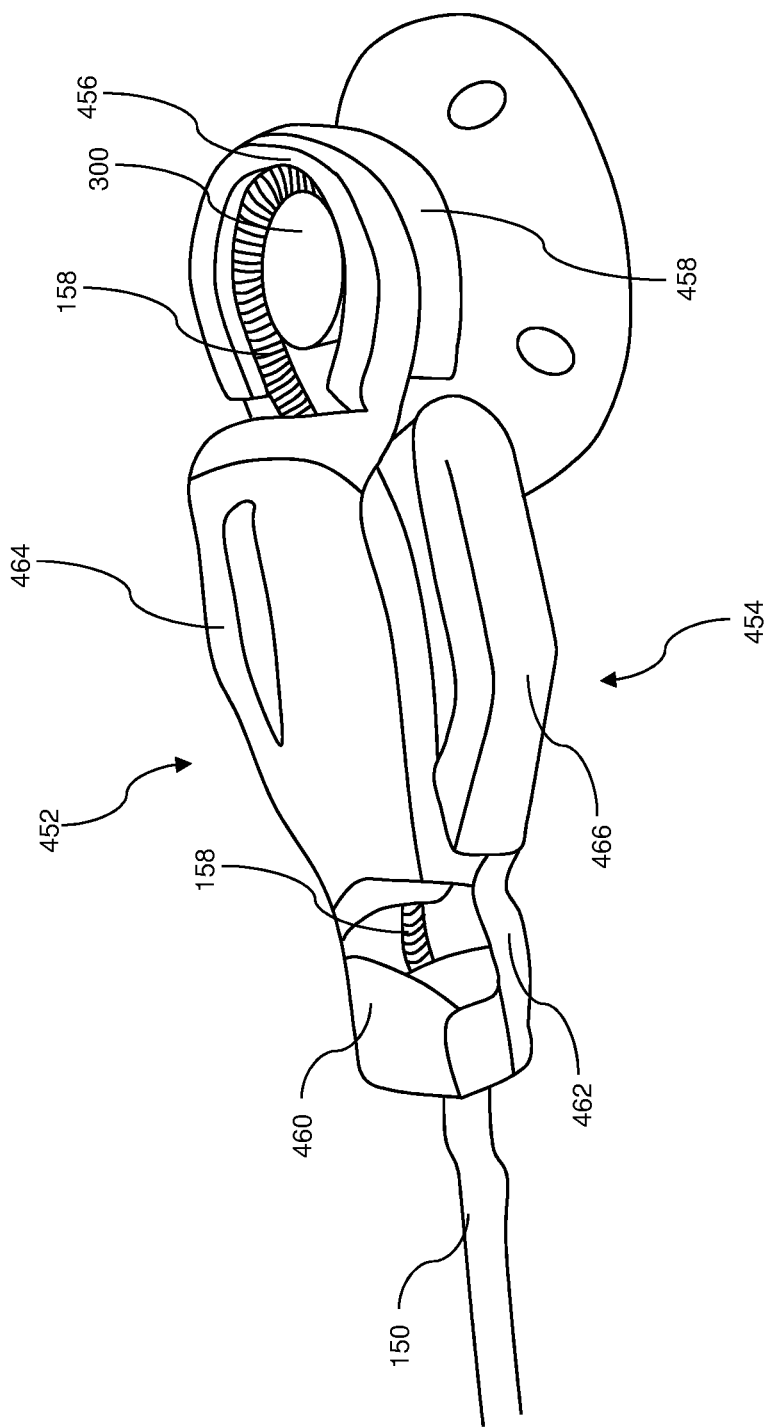
FIG. 10 An exemplary embodiment of the electrode connector of the present invention shown attached to the node of a physiological electrode.

FIG. 10 illustrates yet another embodiment of the present invention, attached to the node of a physiological electrode. Like previous figures, the embodiment of FIG. 10 comprises an upper segment 452 and a lower segment 450. Both segments 450 and 452 are preferably identical in shape and size, the lower segment 450 flipped and underneath the upper segment. Each segment preferably comprises a node section 456 for the upper segment 452, and 458 for the lower segment 450; a pinch section 464 for the upper segment 452, and 466 for the lower segment 450; and a junction section 460 for the upper segment 452, and 462 for the lower segment 450. A cavity (not shown) is preferably located on the underside of the upper segment 452 and the upperside of lower segment 450 such that a connection element 158 can travel through the cavity to mechanically and electrically connect to a lead wire 150 at junction sections 460 and 462 and an electrode node 300 at node sections 456 and 458. As in previously discussed embodiments, the connection element 158 is preferably helical and fills junction sections 460 and 462 due to its internal bias. As pinch sections 464 and 466 are pressed toward each other, the diameter of the opening created by node sections 456 and 458 preferably increases, allowing the connection element 158 to expand and the lead wire connector to be slipped over the electrode node 300. As pinch sections 464 and 466 are released, the diameter of the opening created by node sections 456 and 458 preferably decreases causing the connection element 158 to clamp around the electrode node 300.

It will be apparent to those skilled in the art that various modifications and variations can be made to the present invention as described above without departing from the spirit and scope of the invention. Thus, it is intended that the present invention cover the modifications and variations of this invention provided they come within the scope of the appended claims and their equivalents.

What I claim is:

1. A method for connecting at least one lead wire to an electrode comprising:
    applying a unidirectional or bidirectional force to an expander which in turn applies a multi-directional force to stretch a connection element for receiving a node of a male connector of the electrode;
    placing the connection element for receiving the node of a male connector of the electrode over the node of the male connector of the electrode; and
    releasing the unidirectional or bidirectional force on the expander in order to contract the connection element around the node of the male connector of the electrode,
    wherein the connection element contracts to make contact at least at 5 separate points with the node of the male connector of the electrode.

2. The method of claim 1, wherein the connection element is helical.

3. The method of claim 1, wherein the connection element makes continuous contact with the node of the male connector of the electrode.

4. The method of claim 1, wherein the expander applies a multi-directional force to stretch at least 2 connection elements.

5. The method of claim 1, wherein the electrode is a physiological electrode.

6. The method of claim 1, wherein there is no vector sum of forces on the electrode.

\* \* \* \* \*